(12) United States Patent
Shani et al.

(10) Patent No.: US 12,004,456 B2
(45) Date of Patent: Jun. 11, 2024

(54) METHOD FOR MONITORING WATER STATUS IN A FIELD

(71) Applicant: N-Drip Ltd., Kfar Saba (IL)

(72) Inventors: Uri Shani, Tel-Aviv (IL); Sharon Dabach, Tel-Aviv (IL)

(73) Assignee: N-Drip Ltd., Kfar Saba (IL)

( * ) Notice: Subject to any disclaimer, the term of this patent is extended or adjusted under 35 U.S.C. 154(b) by 985 days.

(21) Appl. No.: 16/959,679

(22) PCT Filed: Jan. 3, 2019

(86) PCT No.: PCT/IL2019/050021
§ 371 (c)(1),
(2) Date: Jul. 2, 2020

(87) PCT Pub. No.: WO2019/135235
PCT Pub. Date: Jul. 11, 2019

(65) Prior Publication Data
US 2021/0076580 A1    Mar. 18, 2021

Related U.S. Application Data

(60) Provisional application No. 62/613,074, filed on Jan. 3, 2018.

(51) Int. Cl.
*G01N 33/24* (2006.01)
*A01G 24/44* (2018.01)
(Continued)

(52) U.S. Cl.
CPC .......... *A01G 25/167* (2013.01); *A01G 24/44* (2018.02); *G01N 19/10* (2013.01); *G01N 33/246* (2013.01); *G01N 2033/245* (2013.01)

(58) Field of Classification Search
CPC .... G01N 27/223; G01N 5/045; G01N 33/246; G01N 27/048; G01N 27/121;
(Continued)

(56) References Cited

U.S. PATENT DOCUMENTS 5,103,654 A   4/1992  Gee et al.
8,051,871 B2 * 11/2011 Shani ................. A01G 25/167
                                                        239/63

(Continued)

FOREIGN PATENT DOCUMENTS

AU    2008246228 A1 *  6/2009  .......... A01G 25/167
BR    102019017799 A2 *  3/2021  .......... A01G 27/003
(Continued)

OTHER PUBLICATIONS

Examination Report Dated Jan. 19, 2023 From the Australian Government, IP Australia Re. Application No. 2019205149. (3 Pages).
(Continued)

*Primary Examiner* — Andre J Allen

(57) ABSTRACT

A system for sensing water status in soil includes a porous material selected for actively proliferating root growth and a water status sensor that is hydraulically coupled to the porous material. The porous material is configured to have an area of at least 0.025 m².

30 Claims, 9 Drawing Sheets

(51) Int. Cl.
*A01G 25/16* (2006.01)
*G01N 19/10* (2006.01)

(58) Field of Classification Search
CPC ...... G01N 25/56; G01N 19/10; G01N 31/222;
G01N 22/04; G01N 5/02; G01N 33/10;
G01N 33/346; G01N 5/025; G01N 15/08;
G01N 5/04; G01N 33/24; G01N 33/383;
G01N 9/36; G01N 21/3554; G01N 33/46;
G01N 15/0893; G01N 27/226; G01N
33/2847; G01N 13/02; G01N 25/62;
G01N 21/81; G01N 25/68; G01N 33/12;
G01N 7/10; G01N 25/14; G01N 33/367;
G01N 33/0098; G01N 5/00; G01N 7/14;
G01N 1/44; G01N 2291/0256; G01N
29/036; G01N 22/00; G01N 27/225;
G01N 9/02; G01N 33/42; G01N 15/0826;
G01N 2291/02845; G01N 25/18; G01N
27/18; G01N 15/082; G01N 33/00; G01N
33/36; G01N 25/64; G01N 3/08; G01N
33/38; G01N 17/00; G01N 33/02; G01N
9/24; G01N 13/00; G01N 27/423; G01N
21/359; G01N 27/043; G01N 1/20; G01N
2015/0873; G01N 29/11; G01N 7/16;
G01N 1/40; G01N 2015/0866; G01N
21/65; G01N 25/66; G01N 27/06; G01N
33/4833; G01N 15/0806; G01N 21/3559;
G01N 21/3563; G01N 21/431; G01N
21/86; G01N 23/16; G01N 25/00; G01N
25/005; G01N 25/58; G01N 27/12; G01N
33/025; G01N 33/26; G01N 33/34; G01N
33/362; G01N 1/405; G01N 13/04; G01N
15/088; G01N 2001/4027; G01N
2021/656; G01N 21/314; G01N 2201/08;
G01N 2291/102; G01N 27/122; G01N
29/022; G01N 29/07; G01N 35/00; G01N
7/04; G01N 1/2214; G01N 2001/1481;
G01N 2009/026; G01N 2033/245; G01N
21/15; G01N 21/33; G01N 21/8507;
G01N 2203/0019; G01N 2203/0282;
G01N 2291/014; G01N 2291/0255; G01N
2291/02818; G01N 27/041; G01N
27/185; G01N 27/42; G01N 33/0006;
G01N 33/04; G01N 1/286; G01N 11/14;
G01N 15/0205; G01N 17/002; G01N
17/02; G01N 19/04; G01N 2009/022;
G01N 2021/8466; G01N 2033/0091;
G01N 21/4738; G01N 21/7703; G01N
2203/0025; G01N 2203/021; G01N
2291/0237; G01N 2291/02441; G01N
2291/0426; G01N 2291/0427; G01N
25/72; G01N 27/046; G01N 27/07; G01N
29/28; G01N 29/30; G01N 31/168; G01N
31/22; G01N 33/0011; G01N 33/222;
G01N 33/241; G01N 35/0099; G01N
7/02; G01N 1/14; G01N 1/34; G01N
17/004; G01N 2001/2021; G01N
2001/2261; G01N 2013/0208; G01N
2033/0093; G01N 21/00; G01N 21/276;
G01N 21/29; G01N 21/552; G01N 21/78;
G01N 21/80; G01N 21/89; G01N
21/8901; G01N 2203/0016; G01N
2203/0039; G01N 2203/0094; G01N
2203/0222; G01N 2203/0676; G01N
2223/613; G01N 2291/0238; G01N
2291/0251; G01N 2291/02827; G01N
2291/02863; G01N 2291/02881; G01N
2291/0422; G01N 2291/2634; G01N
23/09; G01N 25/02; G01N 25/142; G01N
25/48; G01N 27/00; G01N 27/045; G01N
27/126; G01N 27/4166; G01N 27/72;
G01N 29/326; G01N 3/32; G01N 30/00;
G01N 31/221; G01N 33/03; G01N 33/32;
G01N 33/365; G01N 33/442; G01N
33/447; G01N 33/48; G01N 33/5088;
G01N 35/028; G01N 35/04; G01N 1/04;
G01N 1/2035; G01N 15/0618; G01N
2011/0053; G01N 2035/00188; G01N
2035/00217; G01N 2035/0441; G01N
2035/0484; G01N 21/8483; G01N
2291/015; G01N 2291/02854; G01N
2291/044; G01N 23/06; G01N 27/02;
G01N 27/026; G01N 29/2462; G01N
29/42; G01N 29/4418; G01N 3/46; G01N
31/00; G01N 33/0036; G01N 33/007;
G01N 33/06; G01N 33/15; G01N
33/2823; G01N 35/025; G01N 7/00;
G01N 1/00; G01N 1/18; G01N 1/2226;
G01N 1/2273; G01N 1/2294; G01N
1/4005; G01N 1/4055; G01N 11/06;
G01N 11/10; G01N 11/142; G01N
11/165; G01N 15/0272; G01N 15/0631;
G01N 15/0656; G01N 19/02; G01N
2001/2007; G01N 2001/2241; G01N
2001/4083; G01N 2011/0046; G01N
2013/025; G01N 2013/0258; G01N
2013/0283; G01N 2015/0853; G01N
2015/086; G01N 2021/0339; G01N
2021/151; G01N 2021/1706; G01N
2021/354; G01N 2021/3595; G01N
2021/6419; G01N 2021/6421; G01N
2021/6432; G01N 2021/6439; G01N
2021/6441; G01N 2021/7723; G01N
2021/7786; G01N 2033/0003; G01N
2033/0083; G01N 2033/0095; G01N
2035/00336; G01N 2035/00346; G01N
2035/00356; G01N 2035/00495; G01N
2035/00524; G01N 2035/00534; G01N
2035/0097; G01N 2035/0406; G01N
2035/0422; G01N 2035/0424; G01N
2035/0443; G01N 2035/0444; G01N
2035/0455; G01N 2035/0491; G01N
2035/103; G01N 21/07; G01N 21/1702;
G01N 21/251; G01N 21/27; G01N
21/272; G01N 21/274; G01N 21/3151;
G01N 21/35; G01N 21/3577; G01N
21/3581; G01N 21/37; G01N 21/39;
G01N 21/43; G01N 21/47; G01N 21/474;
G01N 21/55; G01N 21/554; G01N 21/59;
G01N 21/64; G01N 21/6428; G01N
21/6447; G01N 21/645; G01N 21/6454;
G01N 21/658; G01N 21/69; G01N 21/76;
G01N 21/94; G01N 2201/0221; G01N
2201/0415; G01N 2201/0621; G01N
2203/0005; G01N 2203/0007; G01N
2203/0017; G01N 2203/0044; G01N
2203/006; G01N 2203/0067; G01N
2207/0075; G01N 2203/0076; G01N
2203/0078; G01N 2203/0092; G01N
2203/0098; G01N 2203/0212; G01N 2203/0218; G01N 2203/0226; G01N
2203/0228; G01N 2203/0236; G01N
2203/0256; G01N 2203/0278; G01N
2203/0284; G01N 2203/0286; G01N
2203/0682; G01N 2203/0688; G01N
2223/01; G01N 2223/04; G01N
2223/205; G01N 2223/505; G01N
2223/616; G01N 2223/633; G01N
2223/636; G01N 2223/643; G01N
2291/011; G01N 2291/0212; G01N
2291/0228; G01N 2291/0231; G01N
2291/02408; G01N 2291/02491; G01N
2291/0253; G01N 2291/02809; G01N
2291/0421; G01N 2291/048; G01N
2291/105; G01N 2291/265; G01N
2291/2698; G01N 23/00; G01N 23/02;
G01N 23/083; G01N 23/12; G01N
23/203; G01N 24/081; G01N 24/085;
G01N 25/04; G01N 25/44; G01N 25/60;
G01N 2500/00; G01N 27/002; G01N
27/023; G01N 27/028; G01N 27/125;
G01N 27/205; G01N 27/221; G01N
27/4065; G01N 27/4146; G01N 27/416;
G01N 27/4162; G01N 27/60; G01N
27/605; G01N 29/02; G01N 29/0609;
G01N 29/0618; G01N 29/227; G01N
29/228; G01N 29/241; G01N 29/2418;
G01N 29/4436; G01N 29/4454; G01N
29/4472; G01N 29/50; G01N 3/00; G01N
3/066; G01N 3/10; G01N 3/30; G01N
3/36; G01N 3/40; G01N 3/42; G01N
3/56; G01N 30/12; G01N 31/005; G01N
31/007; G01N 31/10; G01N 31/229;
G01N 33/0016; G01N 33/0026; G01N
33/0062; G01N 33/1833; G01N 33/28;
G01N 33/2829; G01N 33/2835; G01N
33/2888; G01N 33/343; G01N 33/388;
G01N 33/44; G01N 33/497; G01N
33/5008; G01N 33/5044; G01N 33/5438;
G01N 33/60; G01N 33/68; G01N 33/94;
G01N 35/00009; G01N 35/00663; G01N
35/00693; G01N 35/0092; G01N
35/0098; G01N 35/026; G01N 35/1002;
G01N 7/18; G01N 9/00; G01N 9/06;
G01N 9/08; G01N 9/26; G01N 1/2202;
G01N 1/2258; G01N 11/04; G01N 15/00;
G01N 15/0886; G01N 2001/2223; G01N
2009/024; G01N 2013/0225; G01N
2013/0275; G01N 2021/3148; G01N
21/21; G01N 21/41; G01N 21/6456;
G01N 21/74; G01N 2291/0257; G01N
2291/2697; G01N 23/005; G01N 23/046;
G01N 25/32; G01N 27/28; G01N 27/404;
G01N 27/4045; G01N 27/407; G01N
27/4075; G01N 27/414; G01N 27/82;
G01N 29/24; G01N 29/32; G01N 29/44;
G01N 29/4427; G01N 29/46; G01N
29/48; G01N 30/30; G01N 30/6091;
G01N 31/164; G01N 33/0031; G01N
33/0032; G01N 33/0047; G01N 33/18;
G01N 33/2852; G01N 35/00603; G01N
35/02; G01N 35/085; G01N 35/109;
A01G 25/167; A01G 25/16; A01G
27/008; A01G 7/00; A01G 25/092; A01G
27/003; A01G 13/0268; A01G 23/00;
A01G 27/00; A01G 29/00; A01G 31/00;
A01G 5/06; A01G 7/045; A01G 9/02;
A01G 9/24; A01G 24/00; A01G 24/20;
A01G 9/00; A01G 9/249
USPC .......................................................... 73/73
See application file for complete search history.

(56) References Cited

U.S. PATENT DOCUMENTS

| 8,714,181 | B2* | 5/2014 | Shani | G01N 7/10 |
| | | | | 239/63 |
| 10,274,444 | B2* | 4/2019 | Lestelle | G01N 33/0098 |
| 10,365,196 | B2* | 7/2019 | Gimenez Calbo | G01N 33/246 |
| 11,549,931 | B2* | 1/2023 | Kim | G01N 27/223 |
| 2004/0145379 | A1* | 7/2004 | Buss | G01N 27/223 |
| | | | | 324/664 |
| 2009/0050214 | A1* | 2/2009 | Shani | G01N 7/10 |
| | | | | 239/69 |
| 2009/0133481 | A1* | 5/2009 | Baker | G01N 5/025 |
| | | | | 73/73 |
| 2010/0282859 | A1 | 11/2010 | Helbig et al. | |
| 2019/0366678 | A1* | 12/2019 | Jones | D03D 15/283 |

FOREIGN PATENT DOCUMENTS

| CA | 3034998 | | 3/2017 |
| CN | 1441250 | | 9/2003 |
| CN | 101848634 | | 9/2010 |
| CN | 102621194 | | 8/2012 |
| CN | 115166156 A | * | 10/2022 |
| DE | 102007036018 | | 9/2021 |
| EP | 2508066 | | 10/2012 |
| EP | 2180778 | | 4/2013 |
| JP | 2017221150 A | * | 12/2017 |
| KR | 20200022990 A | * | 3/2020 |
| WO | WO 2019/135235 | | 7/2019 |

OTHER PUBLICATIONS

Communication Pursuant to Article 94(3) EPC Dated Dec. 22, 2022 From the European Patent Office Re. Application No. 19735861.7 (7 Pages).
Communication Pursuant to Article 94(3) EPC Dated Jun. 23, 2022 From the European Patent Office Re. Application No. 19735861.7. (7 Pages).
Communication Pursuant to Article 94(3) EPC Dated Jun. 13, 2023 From the European Patent Office Re. Application No. 19735861.7 (5 Pages).
Examination Report Under Sections 12 & 13 of the Patents Act, 1970 and the Patents Rules, 2003 dated Mar. 21, 2022 From the Government of India, Intellectual Property India, Patents, Designs, Trade Marks, Geographical Indications, The Patent Office Re. Application No. 202027031422. (6 Pages).
Notification of Office Action Dated Mar. 22, 2022 From the State Intellectual Property Office of the People's Republic of China Re. Application No. 201980011505.9 and Its Translation into English . (4 Pages).
Supplementary European Search Report and the European Search Opinion Dated Sep. 15, 2021 From the European Patent Office Re. Application No. 19735861.7. (8 Pages).
Notification of Office Action and Search Report Dated Jun. 24, 2021 From the State Intellectual Property Office of the People's Republic of China Re. Application No. 201980011505.9 and an English Summary of Office Action. (18 Pages).
Office Action dated Mar. 26, 2023 From the Israel Patent Office Re. Application No. 275810. (4 Pages).
International Preliminary Report on Patentability dated Jul. 16, 2020 From the International Bureau of WIPO Re. Application No. PCT/IL2019/050021. (8 Pages).
International Search Report and the Written Opinion dated Apr. 14, 2019 From the International Searching Authority Re. Application No. PCT/IL2019/050021. (14 Pages).

(56) References Cited

OTHER PUBLICATIONS

Bengough et al. "Mechanical Impedance to Root Growth: A Review of Experimental Techniques and Root Growth Responses", Journal of Soil Science, 41(3): 341-358, Sep. 1990.
Bengough et al. "Penetrometer Resistance, Root Penetration Resistance and Root Elongation Rate in Two Sandy Loam Soils", Plant and Soil, 131(1): 59-66, Feb. 1991.
Coelho "Flow and Uptake Patterns Affecting Soil Water Sensor Placement for Drip Irrigation Management", Transactions of the ASAE, 39(6): 2007-2016, 1996.
Dabach et al. "Optimal Tensiometer Placement for High-Frequency Subsurface Drip Irrigation Management in Heterogeneous Soils", Agricultural Water Management, 152: 91-98, Apr. 2015.
Dabach et al. "The Influence of Water Uptake on Matric Head Variability in a Deip-Irrigated Root Zone", Soil & Tillage Research, 155: 216-224, Jan. 2016.
De Tourdonnet et al. "Non-Uniformity of Environmental Conditions in Greenhouse Lettuce Production Increases the Risk of N Pollution and Lower Product Quality", Agronomie, 21(4): 297-309, May-Jun. 2001.
Feddes et al. "Simulation of Field Water Uptake by Plants Using a Soil Water Dependent Root Extraction Function", Journal of Hydrology, 31(1-2): 13-26, Sep. 1976.
Herkelrath et al. "Water Uptake by Plants: I. Divided Root Experiments", Soil Science Society of America Journal, 41(6): 1033-1038, Nov. 1977.
Kaspar et al. "Soil Temperature and Root Growth", Soil Science, 154(4): 290-299, Oct. 1992.
Michelakis et al. "Water Use, Wetted Soil Volume, Root Distribution and Yield of Avocado Under Drip Irrigation", Agricultural Water Management, 24(2): 119-131, Oct. 1993.

\* cited by examiner

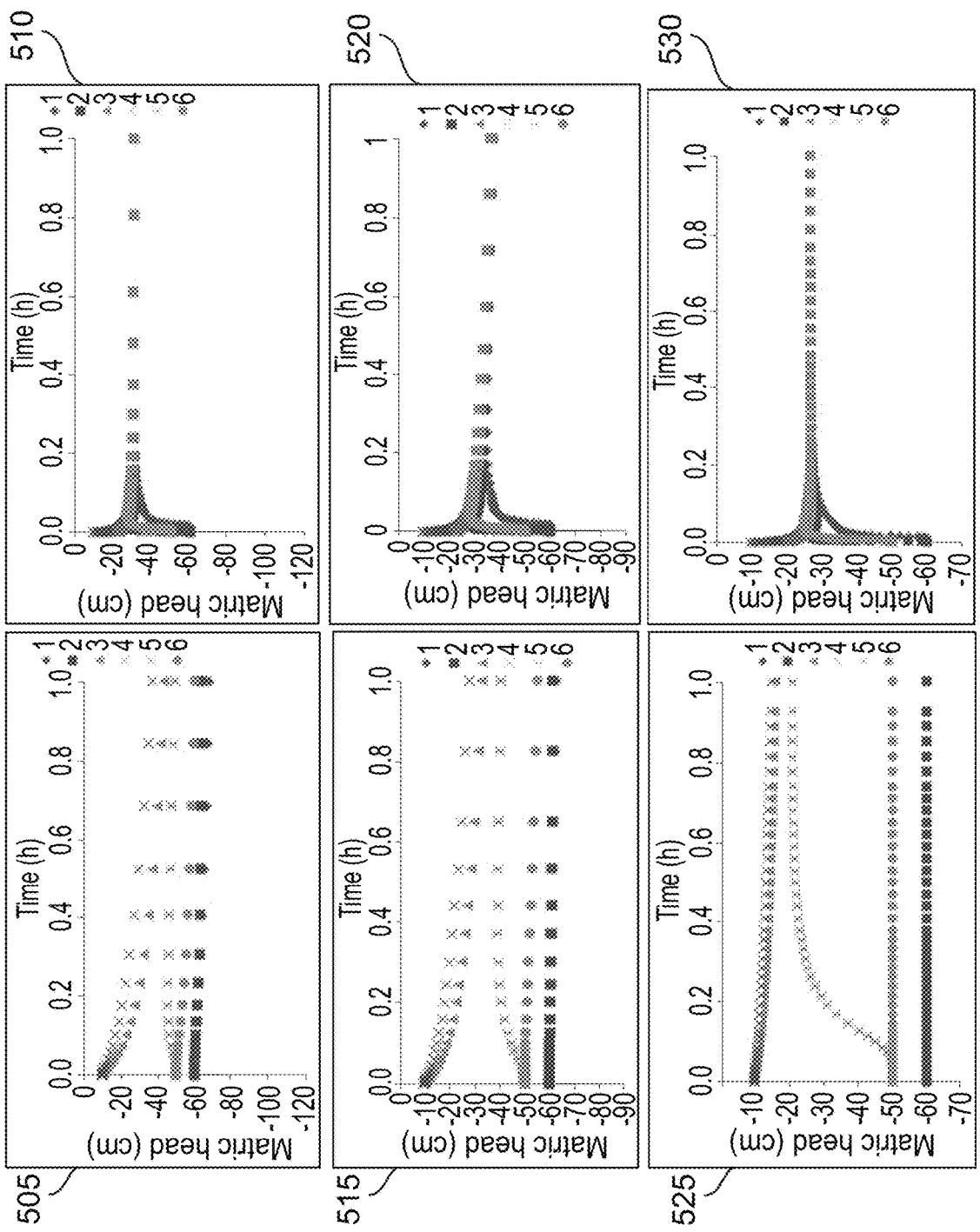

METHOD FOR MONITORING WATER STATUS IN A FIELD

RELATED APPLICATIONS

This application is a National Phase of PCT Patent Application No. PCT/IL2019/050021 having International filing date of Jan. 3, 2019, which claims the benefit of priority under 35 USC § 119(e) of U.S. Provisional Patent Application No. 62/613,074 filed on Jan. 3, 2018. The contents of the above applications are all incorporated by reference as if fully set forth herein in their entirety.

FIELD AND BACKGROUND OF THE INVENTION

The present invention, in some embodiments thereof, relates to sensing of water status in soil and more particularly, but not exclusively, to a device and method to improve spatial coverage when sensing water status in farmland.

Measurement of soil water status is useful for evaluating moisture content of soil, for example, in farmland to determine irrigation scheduling. To measure the water status of the soil, a soil matric potential sensor such as tensiometer or soil water content sensor such as dielectric probe may be used. Typically, these sensors are sensitive to the water status of the soil at a discrete location. However, soil in a natural environment is known to vary significantly both on small and large spatial scales. Spatial variability in the soil may lead to spatial variability in water status measurements.

A representative elementary size (RES) is a known term used in the field of composite materials that corresponds to the volume, area, or length of a sample, necessary to provide measurements, which represent the whole. Measurements made with samples of composite material below the RES may be expected to oscillate. As the sample size is increased toward its RES, the oscillating is expected to dampen out until consistent results may be obtained. Increasing the sample size beyond the RES may lead to additional variations representative of large scale variations in the landscape, e.g. related to changes in topography. Due to the large expected variation in soil, measurements, which do not represent RES might generate high standard deviation values that may not reliably represent status of the soil or the water in the soil.

In a study performed by Efraim Tripler as part of a PhD thesis entitled "Steady state of water and solute in regularly irrigated soil," in 2012 for Hebrew University in Jerusalem, Israel, a field representative elementary length (FREL) that may adequately represent water status in a field with grown plants has been defined. The FREL is defined as a length (in the soil) in which averaging measurements results in similar values everywhere in the FREL.

SUMMARY OF THE INVENTION

Due to the large variability of soil in an agriculture field both in local and field scales it may be difficult to properly assess a state of the water availability to plants growing in a field based on sensor measurements taken in discrete locations in the field. Increasing the number of sensors distributed in the field to improve coverage of the field and increase the probability of measurements being taken near roots of the plants that are being grown may not be practical or economically feasible.

According to an aspect of some example embodiments, there is provided an Averaging Porous Media (APM) that is configured to be positioned in the soil and provide an averaging effect of the water status of the soil on and around which the APM is positioned. According to some example embodiments, the averaging effect is based on defining the APM to have relatively high hydraulic conductivity that encourages internal water flow across the APM. Optionally, hydraulic conductivity is 0.01 to 50 cm/hour or 0.0001 to 50 cm/hour within a matric head range of −500 to 0 cm $H_2O$ respectively.

According to an aspect of some example embodiments, there is provided a method for monitoring water status in a field. According to some example embodiments, an APM is positioned in the soil and water status of soil surrounding the APM is detected based on sensing on the APM with any soil matric potential sensor or soil water content sensor. According to some example embodiments, one senor may be sufficient to determine water status of soil surrounding the APM, e.g. covered or by the APM or within the boundaries of the APM. Optionally, a size and shape of the APM is selected based on an estimated FREL.

According to some example embodiments, the APM is additionally defined to have properties that make it a preferable root growth medium for plants growing in its vicinity. Optionally, the properties defined are mechanical properties of the APM. Optionally, the APM is also impregnated with fertilizer and the nutrients provided by the fertilizer further boost root growth in and around the APM. By encouraging root growth in the APM, sensor measurement taken in the APM may be representative of root water potential of the plants in the vicinity of the APM as well as the soil surrounding the APM. The root water potential of the plants in the vicinity of the APM may include a larger area than the APM dimensions because neighboring plants may grow their roots from an extended distance of another 15-30 cm.

According to some example embodiments, a tensiometer is configured to provide for taking measurements through a flow path that is not obstructed by bubbles. The present inventors have found that measurements, e.g. pressure sensing may be more reliable based on displacing bubbles from the flow path between the porous wall of the tensiometer and a location of sampling the fluid, e.g. water in the flow path.

According to an aspect of some example embodiments, there is provided a system for sensing water status in soil comprising: a porous material selected for actively proliferating root growth and having an area of at least 0.025 $m^2$; and a water status sensor that is coupled to the porous material.

Optionally, the porous material is selected to have a hydraulic conductivity that is higher than the hydraulic conductivity of the soil within a matric head range of 0 to −500 cm $H_2O$).

Optionally, the porous material is selected to have a hydraulic conductivity between 50-0.01 cm/hour within a matric head range of 0 to −500 cm $H_2O$.

Optionally, the porous material is woven geotextile.

Optionally, the porous material is unwoven geotextile.

Optionally, size of pores of the porous material is selected to decrease density of soil when positioned in the soil.

Optionally, the porous material is soaked in a liquid solution in which fertilizer is dissolved.

Optionally, the porous material is impregnated with fertilizer in the form of granulates housed within pores of the porous material.

Optionally, the porous material is impregnated with fertilizer in the form of hydrogel including liquid or granular or slow release fertilizer.

Optionally, the porous material is formed with pockets configured for holding fertilizer.

Optionally, the water status sensor is positioned in a pocket formed in the porous material.

Optionally, the porous material is a strip of material with dimensions of 25-130 cm long and 2-50 cm wide.

Optionally, the water status sensor is soil matric potential sensor or soil water content sensor.

Optionally, the water status sensor is configured to operate without connection to an external water reservoir.

Optionally, the water status sensor is a tensiometer.

Optionally, the soil matric potential sensor comprises: a porous cup; a water filled tube; a sensor; and probe extending from the sensor toward the porous cup.

Optionally, the probe is configured to sample the water at a height below a height at which bubbles accumulate in the water filled tube.

Optionally, the soil matric potential sensor comprises: a porous cup; a water filled tube; a sensor; a bridge shaped channel configured to provide fluid communication between the water filled tube and the sensor, wherein the bridge shaped channel is integrated with a column extending from a peak height of the bridge.

Optionally, the bridge shaped channel is configured to be filled with water.

Optionally, the column is at a height above the sensor.

Optionally, the tube and the bridge shaped channel are integral.

Optionally, the bridge shape channel is shaped as an arc with the column extending from the peak height of the arc or is shaped as an upside down Y.

Optionally, the water status sensor is configured to sense an average reading of the water status over the porous material.

According to an aspect of some example embodiments, there is provided a method for sensing water status in soil comprising: laying a porous material selected for actively proliferating root growth and having an area of at least 0.025 m² on the soil; and hydraulically coupling a water status sensor to the porous material.

Optionally, the porous material is selected to have a hydraulic conductivity that is higher than an average hydraulic conductivity of the soil.

Optionally, the porous material is selected to have a hydraulic conductivity between 50-0.01 cm/hour within a matric head range of 0 to −500 cm H₂O.

Optionally, the porous material is geotextile.

Optionally, the method includes soaking the porous material in a liquid solution or slow release fertilizer in which the fertilizer is dissolved.

Optionally, the method includes impregnating the porous material with fertilizer.

Optionally, the porous material is laid at depth of 5-50 cm under a surface of the soil.

Optionally, the porous material is laid in a row over which cultivated plants are configured to be planted.

Optionally, the porous material is laid over an emitter configured to emit water for irrigating the soil.

Optionally, the porous material is a strip of material with dimensions of 50-130 cm long and 2-50 cm wide.

Optionally, the water status sensor is soil matric potential sensor or soil water content sensor.

Optionally, the water status sensor is a tensiometer.

Optionally, the water status sensor is configured to sense an average reading of the water status over the porous material.

According to an aspect of some example embodiments, there is provided a method for assembling a system for sensing water status in soil, the method comprising: deploying a porous material selected for actively proliferating root growth and having an area of at least 0.025 m² on soil; and coupling a water status sensor to the porous material.

According to an aspect of some example embodiments, there is provided a sheet material configured to sample average water status of soil over a spatial area, the sheet material comprising: a first portion selected to have a hydraulic conductivity between 0.1-0.01 cm/hour within a matric head range of 0 to −500 cm H₂O respectively; and a second portion selected to have a hydraulic conductivity between 50-0 cm/hour within a matric head range of 0 to −50 cm H₂O respectively, wherein the first portion and the second portion are coupled to each other.

Optionally, the first portion and the second portion are formed from two different materials.

Optionally, the first portion is formed based on compacting the sheet material in a roll or in a fold.

Optionally, the sheet material is woven and wherein the first portion has a tighter weave as compared to the second portion.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings and images. With specific reference now to the drawings and images in detail, it is stressed that the particulars shown are by way of example and for purposes of illustrative discussion of embodiments of the invention. In this regard, the description taken with the drawings and images makes apparent to those skilled in the art how embodiments of the invention may be practiced.

In the drawings:

FIGS. 7A and 7B are example graphs for different soils showing matric potential measured over an hour with a soil matric potential sensor and with an APM as described herein respectively.

DESCRIPTION OF SPECIFIC EMBODIMENTS OF THE INVENTION

Figure 1A:
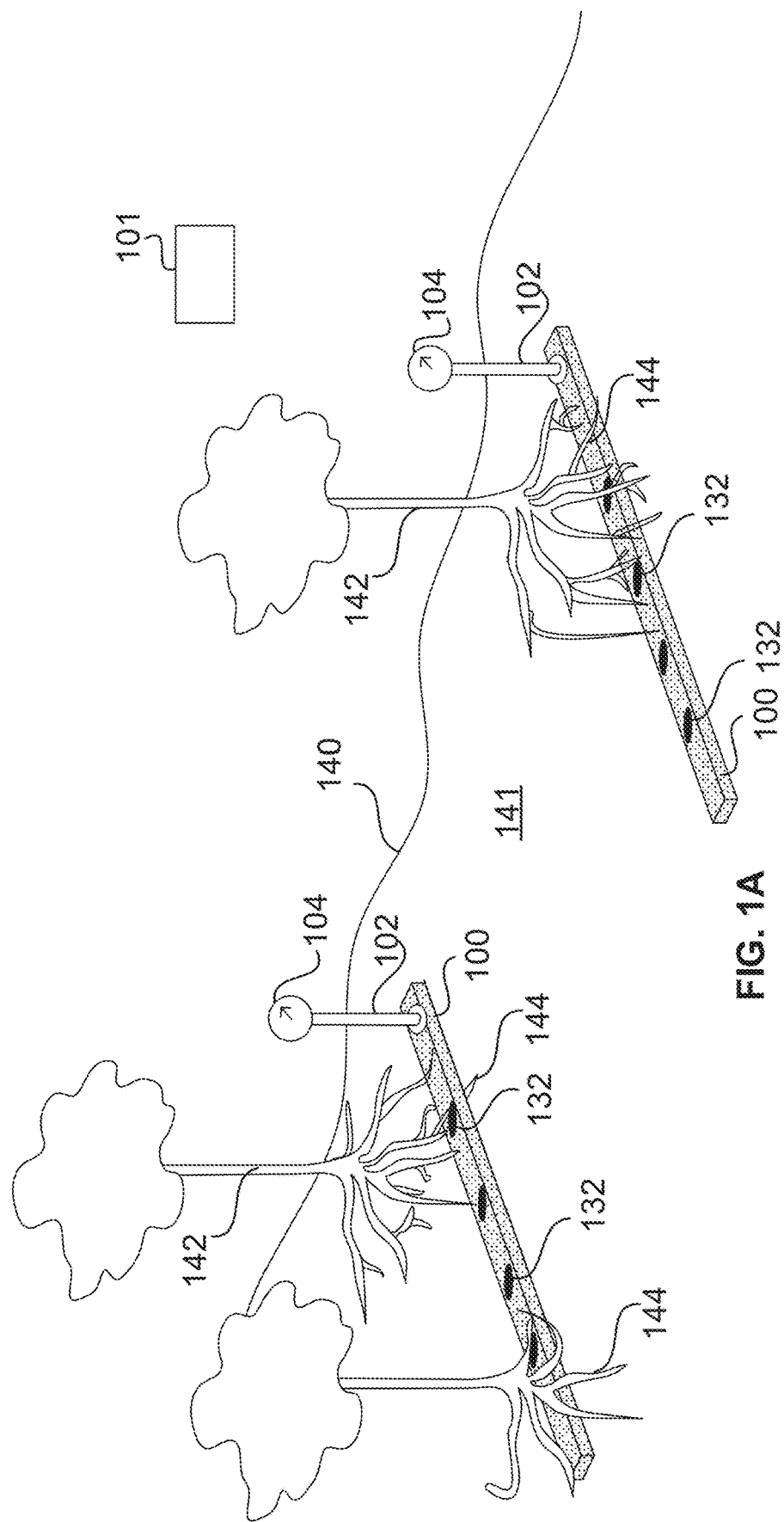
FIGS. 1A and 1B are simplified schematic drawing of two example water status monitoring systems, both in accordance with some example embodiments.

The present invention, in some embodiments thereof, relates to sensing of water status in soil and more particularly, but not exclusively, to a device and method to improve spatial coverage when sensing water status in farmland.

According to some example embodiments, an APM is configured to be formed with a uniform media having a relatively high hydraulic conductivity. In some example embodiments, the hydraulic conductivity is defined to be greater than 0.01 cm/hr when the matric potential is higher than −500 cm $H_2O$. The APM may be made from anyone of a variety of materials including textile, metal or ceramic materials. Where root growth is desired, porous material such as geotextile which may have low mechanical resistance to penetration and growth of roots relative to the soil on which it may be laid is preferred. The geotextile, when selected may be woven or unwoven geotextile.

According to some example embodiments, the APM is positioned on the soil at a depth of 5-50 cm below a surface of the soil. The APM may typically be defined to have an elongated shape. Optionally, the APM defined to be between 0.5 and 2 meters long, e.g. 1 meter long. Optionally, the APM is rectangular in shape and has a width that is 10-50 cm wide. In the examples, the APM may be shaped as a square, circular, cylinder or other shape. In some example embodiments, dimensions of the APM are defined based on a FREL. Optionally, a single APM strip may be selected to have a first area with a relatively high hydraulic conductivity while wet and a second area with a relatively low hydraulic conductivity while wet. The first and second area or zones may be physically and/or hydraulically coupled to each other, e.g. positioned side to side or positioned one over the other. Optionally, the combinations of the low and high hydraulic conductivity areas may provide improved readings over a larger matric head range. Low and high hydraulic conductivity areas may be obtained with different materials, different weaving or based on compressing a portion of an APM, e.g. rolling or folding a portion of the APM.

Aeration provided by the porous material of the APM as described herein together with nutrients that may be provided with fertilizer may encourage root growth on the APM from which soil water matric potential or water content is sensed. By actively encouraging intensive root growth on the APM, the relevance of the soil water status detected may be improved. The improvement may be achieved without the need to actively locate an area including roots.

Optionally, fertilizer may be impregnated in the APM in liquid or solid form. For example, the APM may be soaked in the liquid including the fertilizer. In other examples, the fertilizer may be granular and may be embedded in porous surface of the APM. Optionally, the APM is formed with one or more compartments to house the fertilizer.

In some example embodiments, the APM is configured to have an elongated shape that covers an extended area and a plurality of different soil types and conditions.

In some example embodiments, the APM is positioned to physically contact emitters in the irrigation pipes that provide water to the plants.

Based on contact established between the APM and the roots, the measurements taken on the APM with the sensor may be sensitive to changes in the water potential produced by water intake by the roots and replenishing from the irrigation pipe emitters.

As used herein the term emitter may refer to any of the various types of devices used in an irrigation system to divert water from an irrigation pipe in an irrigation system and deliver the diverted water to the plants, such as drippers or sprinklers. Optionally, water emitter from emitter may be at least partially absorbed by the APM.

Measurement of the water status may, among other things, be used to monitor and manage irrigation.

In some example embodiments, a tensiometer is used to measure the water status in the APM. One known drawback associated with using tensiometers is the false readings that may be obtained due to presence of bubbles in the tensiometer. Bubbles may form for example, when the tensiometer is not completely sealed. Suction by the tensiometer draws air into the tensiometer. The pressure within the tensiometer in this case may be equal to the atmospheric pressure and the water status measurement may not represent the actual water status in the APM or in the soil. Providing a good seal for the tensiometer and all connections to the tensiometer may help prevent bubble formation. Another source of bubbles may be due to water in the soil that may contain dissolved air. As the soil dehydrates, pressure in the tensiometer drops and air dissolved in the water received in the tensiometer may form bubbles. The bubbles may affect the measurements and lead to false readings. The present inventors have found that the adverse effect that the presence of bubbles have on the measurement is greater while the bubbles block the flow path between a porous membrane of the tensiometer and the measuring instrument, e.g. the pressure sensor.

In some example embodiments, a measuring instrument, e.g. pressure sensor is fluidly connected to a body of a tensiometer via a bridge shaped, e.g. an arc shaped or upside down Y shaped channel that includes a column or chimney around the vicinity of a peak height of the bridge. Bubbles may be configured to accumulate in the column without obstructing the flow path to the measuring instrument through the arc shaped channel.

In some other example embodiments, false reading due to bubbles may be avoided based on connecting an elongated probe from the measuring instrument, e.g. the pressure sensor of the tensiometer into the volume of the tensiometer housing. Measurements may be made based on samples obtained at a distal end of the probe. The distal end of the probe may be positioned in a lower portion of the tensiometer housing while the bubbles tend to accumulate in an upper region of the tensiometer housing. In this manner, the flow path between the APM and the measuring instrument does not include bubbles.

Figure 1B:
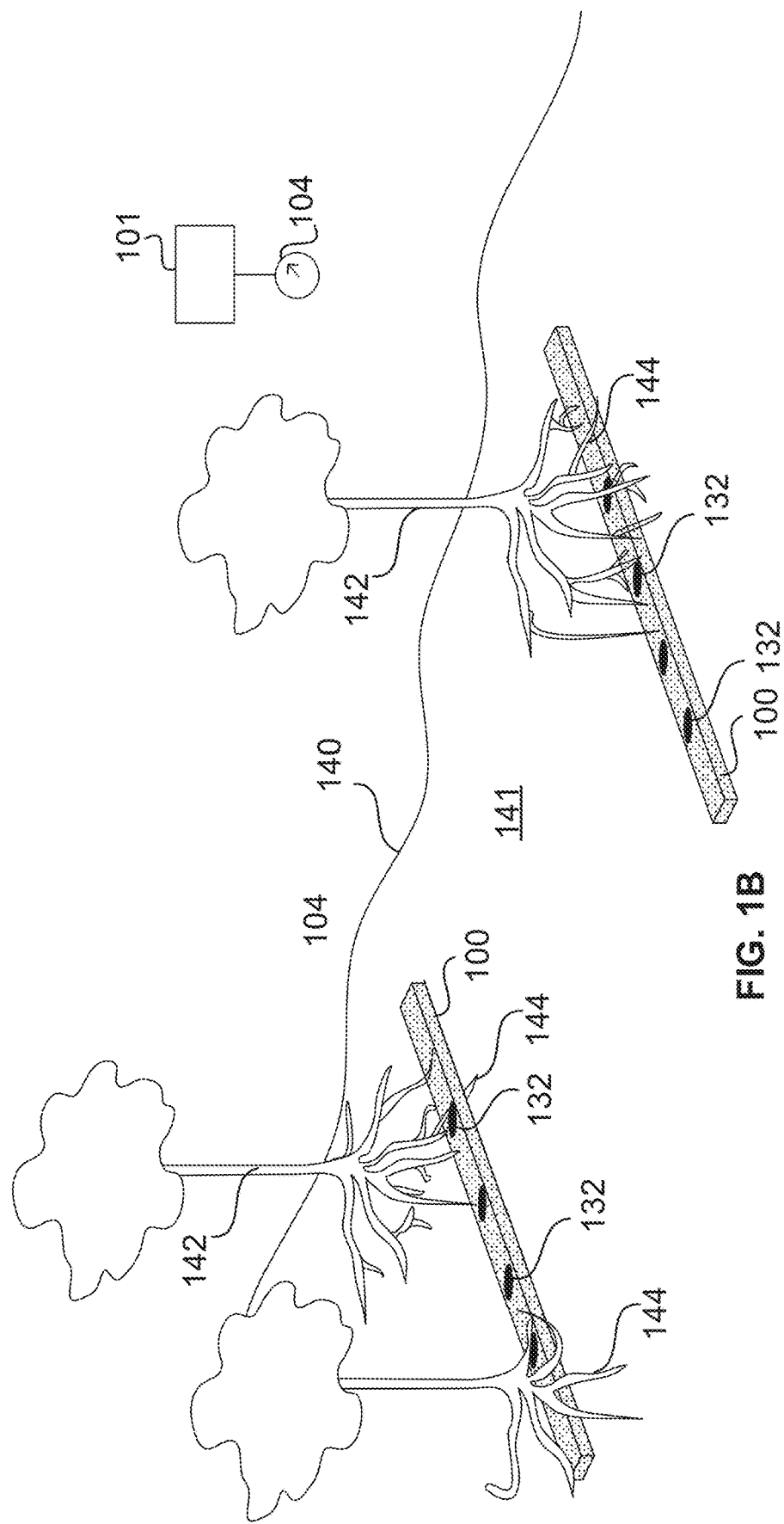

Reference is now made to FIGS. 1A and 1B showing simplified schematic drawings of two example water status monitoring systems, both in accordance with some example embodiments.

According to some example embodiments, a water status monitoring system includes one or more APM 100 spread across a field 140 and a water status sensor 104 positioned on or in proximity to each APM. The water status sensor may be for example a soil matric potential sensor such as tensiometer or soil water content sensor such as dielectric probe. A probe 102 (FIG. 1A) may be positioned directly on APM 100 and may sense the water status of APM 100. Optionally, probe 102 may be positioned in proximity to APM 100, e.g. within 0-5 cm of APM with no physical contact between probe 102 and APM 100. Output from sensors 104 may be transmitted by wired or wireless transmission to a controller 101. In some example embodiments, sensor 104 may be configured to sense the water status of APM 100 remotely (FIG. 1B), e.g. sensor 104 may be a ground penetrating radar sensor.

Output from sensors 104 may be used by controller 101 to control scheduling of irrigation of plants 142. Optionally, controller 101 may adjust location, frequency, duration and timing for irrigation based on input received from sensors 104. Water status sensor 104 need not be connected to an external water reservoir.

In some example embodiments, APM is embedded in a field 140 including cultivated plants 142, e.g. row crops. Optionally and preferably, APM 100 is positioned at a depth of 5-50 cm from surface 140 of the field and may be laid down so that it is substantially parallel to the soil surface 140. In some example embodiments, APM 100 is laid down in rows prior to planting and the seeds or plants 142 are positioned over APM 100. When a field is already planted, APM 100 may be positioned at some distance from the plant row to avoid damaging the roots. Over time, the roots may be expected to grow toward APM 100 due to the preferred conditions that APM 100 provides. APM 100 may be formed from sheet material that is cut to a desired length. Alternatively, APM 100 may be other shapes, e.g. may be cylindrical or disk shaped.

According to example embodiments, APM 100 is formed from a porous material with a relatively high hydraulic conductivity in relation to soil 141, e.g. 0.01 to 50 cm/hour or 0.0001 to 50 cm/hour within a matric head range of $-500$ to 0 cm $H_2O$ respectively. The porosity of the material may be selected to achieve a desired hydraulic conductivity across APM 100. The APM may be made from anyone of a variety of materials including textile, metal or ceramic materials. In some example embodiments, the APM is geotextile, e.g. woven or unwoven. Optionally, porosity of APM 100 is also selected to increase aeration of the soil in the field 140 to improve penetration of oxygen and also to ease penetration of roots by reducing density of the soil.

Due to the relatively high hydraulic conductivity of APM 100, water in the vicinity of APM 100 may quickly and evenly spread across APM 100. This creates an averaging effect of the water status around APM 100 regardless of any variation in the soil on which APM 100 is overlaid. Furthermore, due to the size of APM 100, APM 100 may spread over a plurality of plants and their roots. This may create an averaging effect of the water status over a plurality of plants. Measurements taken with each sensor 104 may represent an average reading for an area covered by APM 100. Since APM 100 is configured to create an averaging effect, only one sensor 104 per APM 100 may be needed.

According to some example embodiments, APM 100 may have an elongated shape with a length of 25-130 cm, e.g. 1 m. In other examples APM 100 may be longer than 130 cm and may reach a length of 2-5 m, e.g. 3-4 m or 3 m. A width of an elongated APM 100 may correspond to a width of a planting row, e.g. 2-50 cm or 20-50 cm. Optionally, an FREL or a field representative elementary area (FREA) is determined and dimensions of APM 100 may be defined based on these parameters.

In this manner a single sensor 104 may be used to manage irrigation over a large area and for a plurality of plants. APM 100 may optionally be laid out in a random or pseudo random pattern. Alternatively, APM 100 may be laid out at defined intervals that substantially cover a planted field. In some example embodiments, water status of a field that is 10-20 hectares may be monitored with only 3-4 APMs each including one sensor 104. Larger fields, e.g. larger than 20 hectares may use 5-7 APMs for water status management. The number of APMs needed may depend on the variability of the field and optionally on the variability of the plants. In some examples it may be assumed that larger fields have larger variability, and therefore may require more sensors. Alternatively, it may be determined or assumed that the soil quality is relatively uniform and less APMs may therefore be required.

According to some example embodiments, APM 100 is additional impregnated with nutrients, e.g. fertilizer for plants 142. The nutrients may be embedded in APM 100 either in liquid or granular form. In some examples, dedicated pockets 132 may be formed in APM 100 that are configured to hold the fertilizer. Optionally, pockets 132 are configured to hold grains of fertilizer or hydrogel with fertilizer for slow release of the fertilizer. Alternatively, fertilizer may be simply spread over APM 100 once APM 100 is positioned on soil 141. The fertilizer may be for example salts such as KCl, DAP, $NH_4NO_3$. According to some example embodiments, the APM 100 promote growth of root 144 in and out of APM 100 due to the available fertilizer, low resistance to growth, and oxygen availability provided by APM 100. Optionally APM 100 is shaped to have ample surface area for substantial root growth. By promoting root growth, a high density of roots 144 in APM 100 may be achieved. The presence of roots 144 may have a significant impact on the water content and potential in APM 100, and may also contribute to reducing variations in measurements that would otherwise occur if discrete measurements were taken at different points covered by APM 100.

Figure 2:
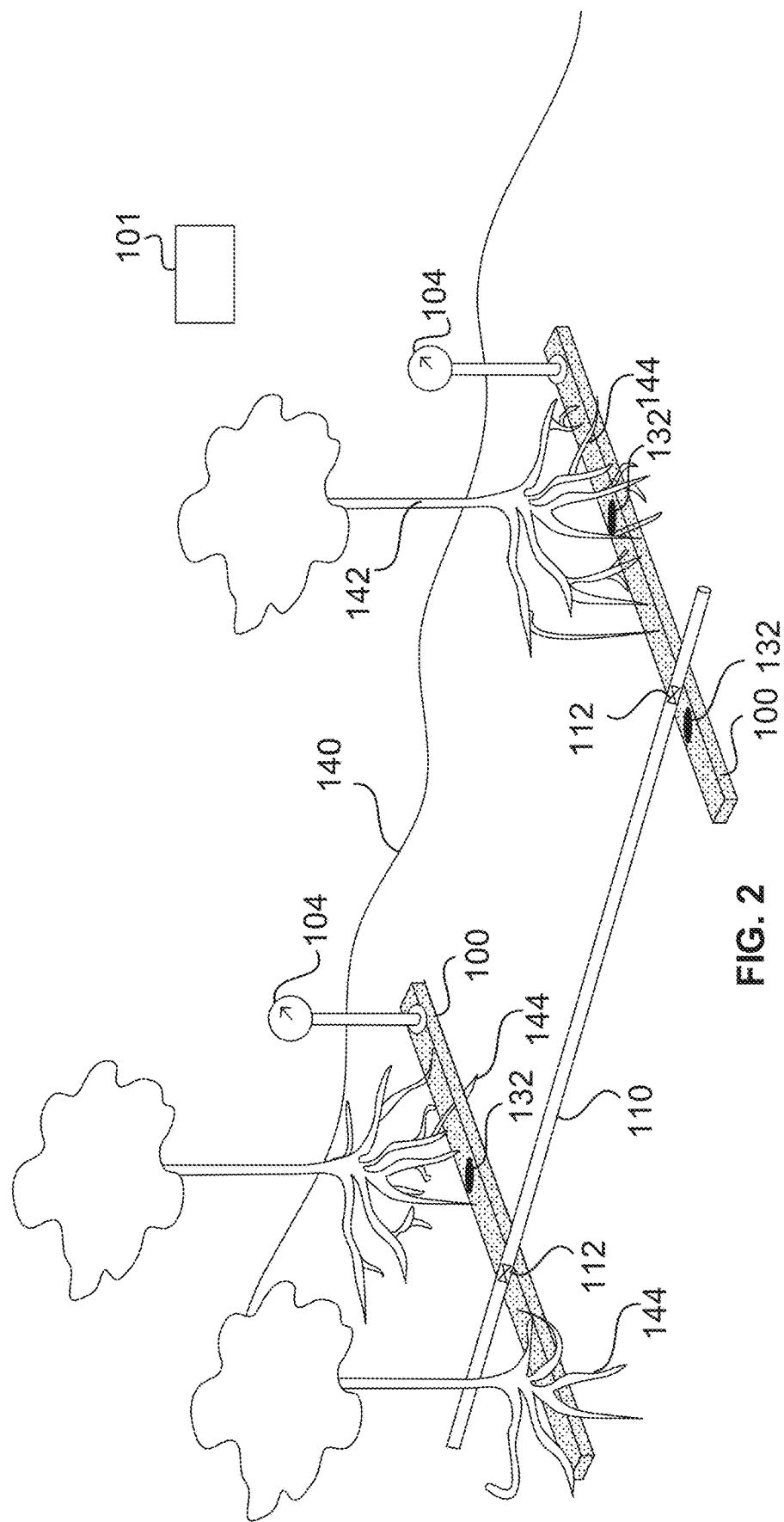
FIG. 2 is a simplified schematic drawing of a water status monitoring system integrated with an irrigation system in accordance with some example embodiments.

Reference is now made to FIG. 2 showing a water status monitoring system integrated with an irrigation system in accordance with some example embodiments. In some example embodiments, APM 100 may be laid out in soil 141 along cultivated plants 142 and may also extend toward irrigation channels or pipes 110 embedded in a field for irrigating soil 141. Optionally, APM 100 may be aligned with emitters 112 in irrigation pipes 110. Controller 101 may receive input from one or more sensors 104 and based on the input controller 101 may control irrigation via irrigation pipes 110 and emitters 112.

Figure 3:
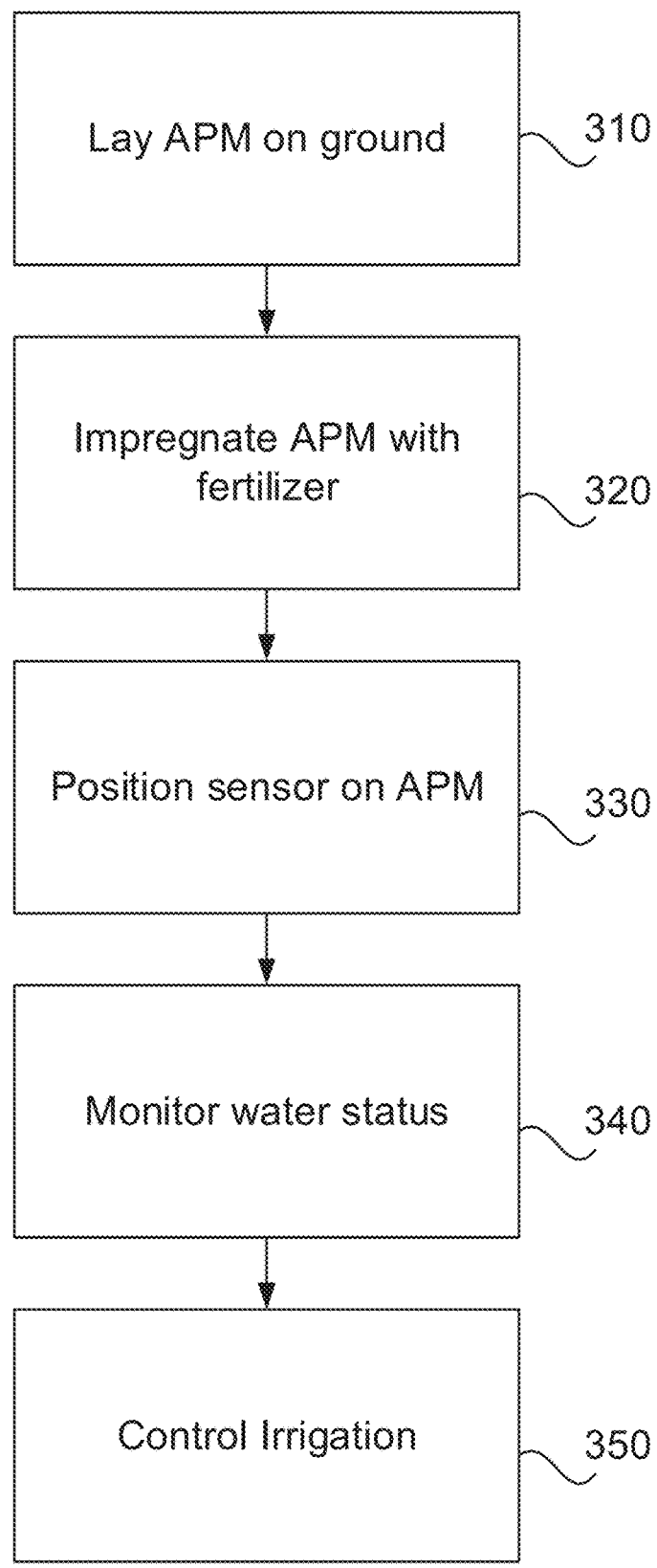
FIG. 3 is a simplified flow chart of an example method to monitor water status of soil near roots of cultivated plants in accordance with some example embodiments.

Reference is now made to FIG. 3 showing a simplified flow chart of an example method to monitor water status of soil near roots of cultivated plants in accordance with some example embodiments. According to some example embodiments, an APM is laid down on a field for cultivating plants (block 310). In some example embodiments, the APM is embedded in the soil at a depth of 5-50 cm. Optionally, the APM may be positioned in ditches or rows in a field that are laid out for planting. In some example the APM is a strip of material having a length of 70-130 cm and width of 2-50 cm. Length of the APM may correspond to a calculated length or otherwise a determined FREL. The strip of material may be for example a woven or otherwise porous strip of geotextile. The strip of material may be otherwise formed from other textiles, metal or ceramic materials. Optionally, a shape and/or orientation of the strip of material is configured to cover a defined area that may potentially include a plurality of different types of soil and may also include or be in a vicinity of the irrigation emitter. Typically, a plurality of APMs is spread in a field.

In some example embodiments, APM, e.g. the strip of material may be impregnated with fertilizer (block 320). Impregnation may be before or after laying down APM. In some example embodiments, impregnation may be by soaking the APM in liquid including fertilizer or by embedding granular fertilizer in a porous surface of the APM. Impregnation may also be by filling one or more dedicated pockets in the APM with granular fertilizer or with hydrogel including fertilizer. Alternatively, the fertilizer may not necessarily be impregnated in the APM but rather spread over the APM after the APM is positioned in the soil. Optionally, the fertilizer may be spread under the APM prior to positioning the APM in the soil.

According to example embodiments, a water status sensor is positioned on the APM so that its probe or wick is in physical contact with the APM. The water status sensor may be for example a soil matric potential sensor such as tensiometer or soil water content sensor such as dielectric probe. The sensor may be positioned anywhere along APM as the water status is expected to be uniform across the APM. Optionally, the sensor is positioned at a defined distance from an edge of the APM, e.g. at least 0-5 cm from the edge. Optionally, the sensor is positioned in compartment or pocket formed in the APM, e.g. a dedicated compartment. Alternatively, the sensor may not be in physical contact with the AMP and soil may fill the gap between the sensor and the APM. In some example embodiments, a portion of the APM may be fitted into a compartment of the sensor.

The soil water status may be monitored based on the sensor readings (block 340). Sensor readings may be transmitted by wireless or wired connection to a central controller. Optionally, the central controller is cloud based. Based on the monitoring, an irrigation recommendation may be provided to a farmer based on which the farmer may control the irrigation (block 350).

Irrigation management may be controlled with an irrigation controller that receives feedback from the sensors in the field and according to the information they supply, decide on opening and closing an irrigation tap or activating an irrigation emitter. In general, the irrigation tap may be opened when the reading of one or two or any number or all of the sensors or the average of the sensors falls below a threshold value. The irrigation may be carried out for a fixed period of time or water volume.

Figure 4A:
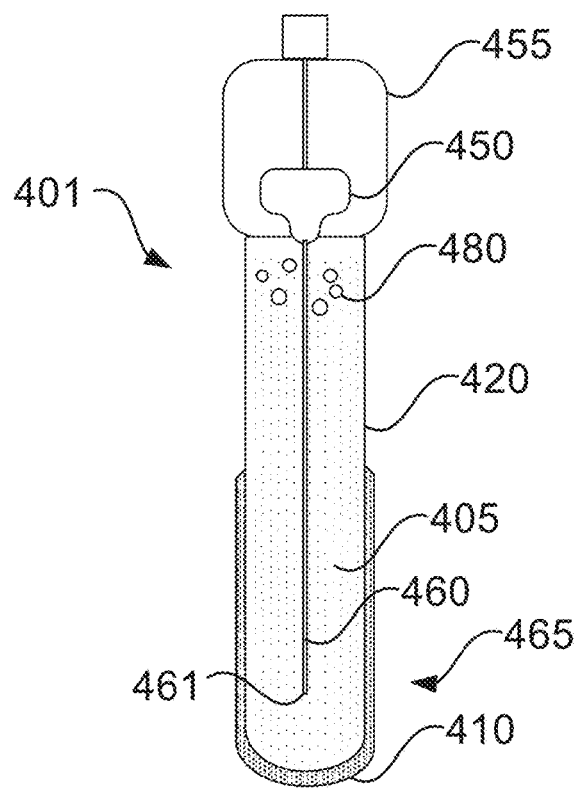
FIGS. 4A and 4B are simplified schematic drawings of two example tensiometers in accordance with some example embodiments.
Figure 4B:
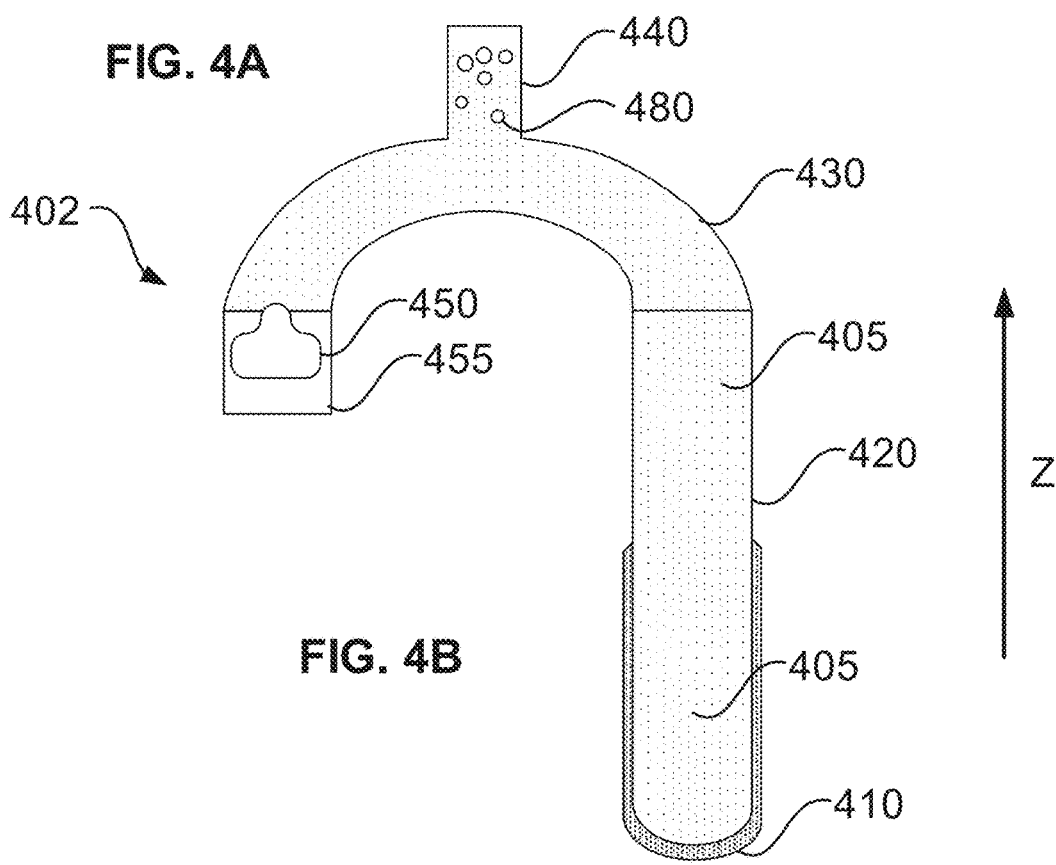

Reference is now made to FIGS. 4A and 4B showing simplified schematic drawings of two example tensiometers in accordance with some example embodiments. In FIG. 4A, a tensiometer 401 includes a porous cup 410, a tube 420 filled with water 405, a sensor head 455 including a sensor 450 and a probe or needle 460 including an inlet at its distal end 461 through which water may enter. Probe 460 includes a central drill through which hydraulic communication may be established between a water reservoir of sensor 455 and water 405. Probe 460 may have an elongated shape and may be configured to extend from sensor 450 toward a bottom portion 465 of tensiometer 401 including porous cup 410. Optionally, bottom portion 465 is a lower half of tensiometer 401. According to some example embodiments, probe 460 is configured provide hydraulic communication with a bottom portion 465 while bubbles 480 formed in tensiometer 401 are expected to accumulate at an upper portion of tensiometer 401. In this manner, flow path of water between an inlet into probe 460 through distal end 461 and porous cup 410 is not obstructed by bubbles 480. The present inventors have found that the adverse effect that bubble formation has on the measurements made with sensor 450 may be reduced, e.g. significantly reduced by a volume between porous cup 410 and inlet through probe 460 that is clear from bubbles 480. Optionally, sensor 450 is a pressure sensor.

FIG. 4B, shows another embodiment for a tensiometer 402. Tensiometer 402 includes porous cup 410, tube 420 filled with water 405, an arc shaped channel 430 including a column (or chimney) 440 and a sensor head 455 including a sensor 450. Sensor 450 may be installed at one end of arc shaped channel 430 and tube 420 may be installed or integrated at an opposite end of arc shaped channel 430. Arc shaped channel 430 may be configured to form a peak in the vertical direction (Z direction) with column 440 also extending in the vertical direction integrated near or at the peak. Arc shaped channel may be filled with water 405. In some example embodiments, bubbles 480, e.g. air bubbles may be expected to rise in column 440 since it is the highest point. By trapping bubbles 480 in column 440, the arch shaped flow path between tube 420 and sensor 450 may be cleared or substantially cleared from bubbles 480. Optionally, measurements made with sensor 450 are more reliable based on clearing bubbles 480 in the flow path between ceramic cup 410 and sensor 450. Optionally, arc shaped flow path may be replaced by alternate shapes such as upside down Y shape.

Figure 5A:
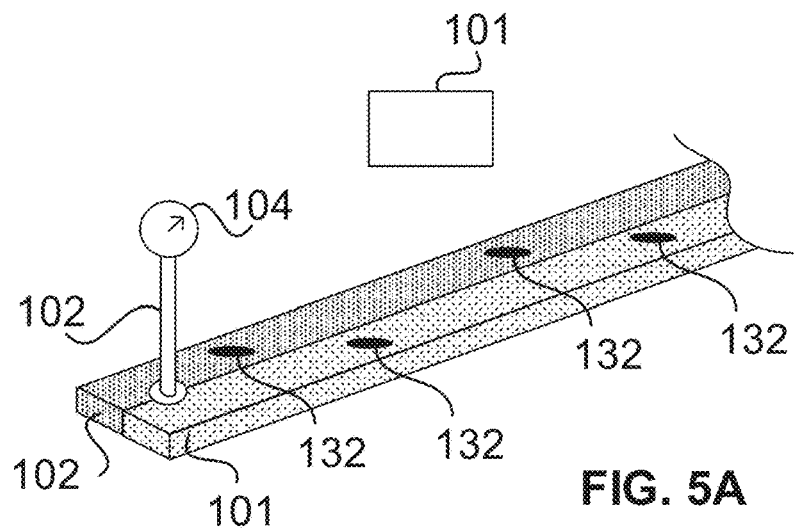
FIGS. 5A, 5B and 5C are simplified schematic drawings of three example water status monitoring systems including two different hydraulic conductivity zones, all in accordance with some example embodiments.
Figure 5B:
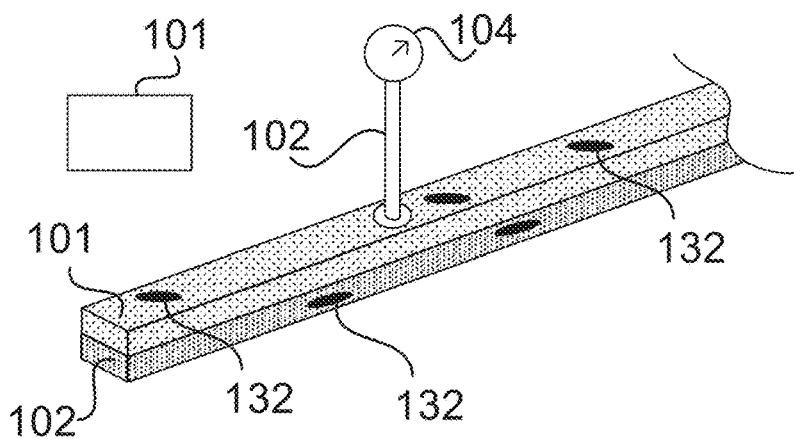
Figure 5C:
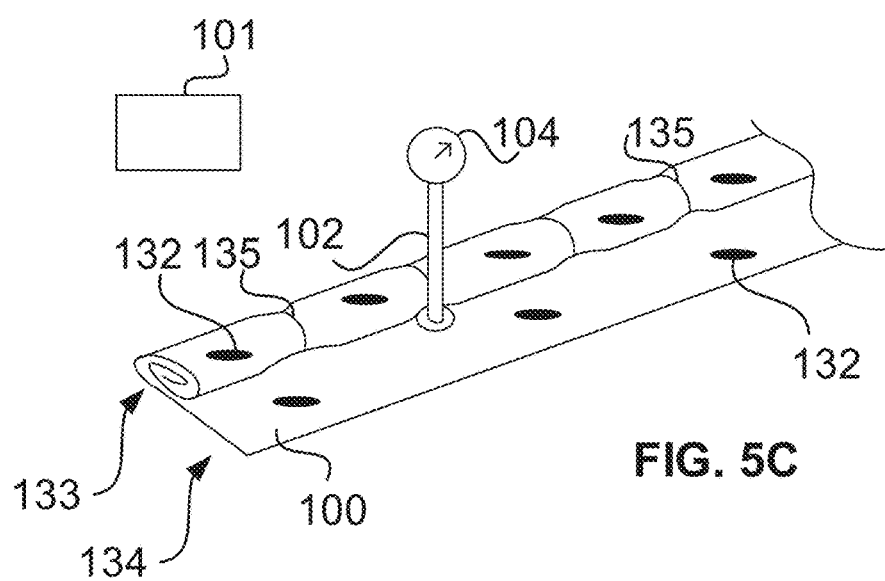

Reference is now made to FIGS. 5A, 5B and 5C showing simplified schematic drawings of three example water status monitoring systems including two different hydraulic conductivity zones, all in accordance with some example embodiments. In some example embodiments, water status monitoring system includes a first APM 101 selected to have a relatively high hydraulic conductivity when wet and a second APM 102 selected to have much lower hydraulic conductivity when wet. Lower hydraulic conductivity of second APM 102 may be achieved with a tighter weave (for a woven APM) or with denser material as compared to first APM that may be formed with a loose weave or more airy material. The first APM 101 and the second APM 102 may be coupled side to side (as shown FIG. 5A) or top to bottom (as shown in FIG. 5B). In FIG. 5B first APM 101 is on top of second APM 102. In other examples, second APM 102 may be on top of first APM 101. Hydraulic conductivity of first APM 101 may drop dramatically fast when water content decreases while hydraulic conductivity of second APM 102 may have a more stable hydraulic conductivity that decrease at a much slower rate with a decrease in water content.

Referring now to FIG. 5C, in some example embodiments, a same APM 100 may be used to form two different hydraulic conductivity zones. Optionally, a low hydraulic conductivity zone may be formed based on compressing a portion of APM 100, based on rolling, folding or crumpling APM 100 together and tying or otherwise confining APM 100 to be close together. Rolled portion 103 that is tied may form a low hydraulic conductivity portion that may have properties similar to those described in reference to APM 102 while a spread out portion 104 of APM 100 may have properties similar to those described in reference to APM 101. Rolled portion 103 is shown to be side to side with the spread out portion 104 of APM 100. Alternatively, rolled portion 103 and spread out portion 104 may be one over the other.

In some example embodiments, probe 102 may be positioned between APM 101 and APM 102 (or between zone 103 and 104) so that sensor 104 may provide a reading from both APMs (or zones). Optionally, probe 102 with sensor 104 may be positioned in a pocket formed between the two APMs (or zones). In other example embodiments, probe 102 with sensor 104 may be positioned on APM 102 (or zone 103) having the lower conductivity so that the entire range may have water flow to sensor 104.

In some example embodiments, APM 101 or APM 100 in zone 104 may have a hydraulic conductivity that changes from 50 to close to 0 cm/h in a matric head range of 0 to −50 cm. APM 102 or APM 100 in zone 103 may have a hydraulic conductivity that changes from 0.2 to 0.01 cm/h in a matric head range of 0 to −500 cm. Although, the low hydraulic conductivity portion and the high hydraulic conductivity portion are coupled to each other and may have an average matric head in the soil they sample, each may operate better at different parts of the matric head range. For example, while the soil is wet (0 to −50 cm $H_2O$) and hydraulic conductivity is relatively high, APM 101 (or zone 104) may average the soil better. While the soil is relatively dry (<<−50 cm $H_2O$), APM 102 (or zone 103) may average the soil better.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Figure 6A:
FIGS. 6A and 6B are example images showing roots of a sunflower grown into a geotextile with sandy soil and loess soil respectively.
Figure 6B:

Reference is now made to FIGS. 6A and 6B showing example images of roots of a sunflower grown into a geotextile with sandy soil and loess soil respectively. As can be seen from the images, the geotextile landfill creates an area that may be used for root growth in different types of soil. As can be seen, roots in a vicinity of the geotextile sphere found their way toward the geotextile penetrated therein. As such, the geotextile created a volume of soil with high root density. By encouraging root growth in the APM, the matric head/water content sensed based on the methods described herein may be affected by the roots more than by the hydraulic properties of the soil as is desired.

Reference is now made to FIGS. 7A and 7B showing example graphs for different soils showing matric potential measured over an hour with a soil matric potential sensor and with an APM as described herein respectively. Each of graphs 505, 510, 515, 520, 525 and 530 shows a change in matric head measured over an hour as measured by five points. The matric head was measured with standard ceramic tensiometer. Graph 505 represents measured change in matric head in clay type soil as measured without an APM strip as described herein. In comparison, graph 510 represents measured change in matric head in same clay type soil including an APM strip. The APM strip used was a non-woven geotextile strip that was 1 meter long and had a density of 500 gm/m² or other density that provides hydraulic conductivity of 0.01-50 cm/hour within a matric head range of −500 to 0 cm $H_2O$, respectively.

Graph 515 represents measured change in matric head in loess type soil as measured without an APM strip as described herein. In comparison, graph 520 represents measured change in matric head in same loess type soil including a geotextile strip as described herein.

Graph 525 represents measured change in matric head in sand type soil as measured without an APM strip as described herein. In comparison, graph 530 represents measured change in matric head in same sand type soil including a geotextile strip as described herein.

As can be seen by the graphs in FIG. 7B measured with the APM, the high hydraulic conductivity of the APM lead to quick transportation of the water and uniform spread, creating an area where the matrix or moisture content is more uniform than the soil outside the strip.

Figure 8:
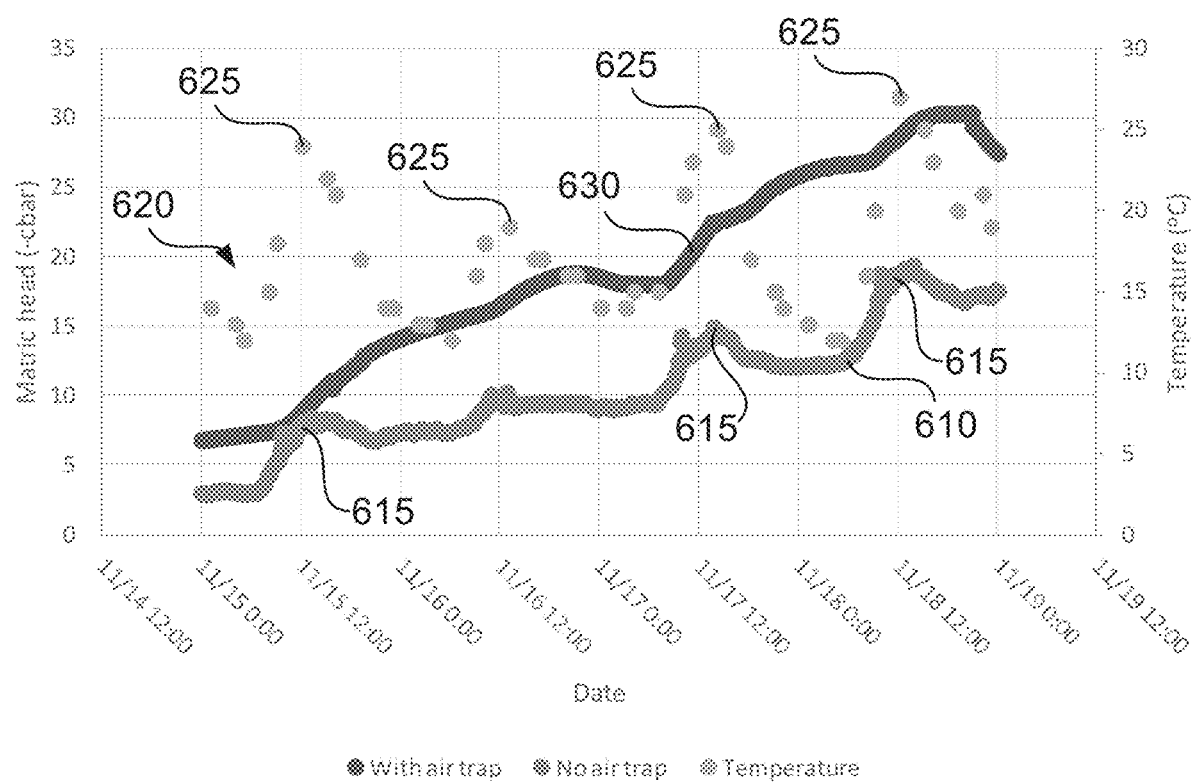
FIG. 8 is an example graph of matric potential measurements for a first tensiometer without a bubble trap and a second tensiometer with a bubble trap as well as ambient temperature measurements for both tensiometers.

Reference is now made to FIG. 8 showing an example graph of matric potential measurements for a first tensiometer without a bubble trap and a second tensiometer with a bubble trap as well as ambient temperature measurements for both tensiometers. Measurements shown were taken over a five day period. Curve 610 is an example graph of matric potential for the first tensiometer without a bubble trap. The first tensiometer is a tensiometer as known in the art. Dots 620 correspond to ambient temperature measurements taken for both tensiometers. As can be seen, the temperature measurements include a series of peaks 625 or a rising in temperature. The sharp increases in temperature recorded are due to bubbles trapped in the first tensiometer. The matric potential readings also show waves or peaks 615 when a bubble is present. Curve 630 is an example graph of matric head for the second tensiometer without a bubble trap. The second tensiometer is similar to the tensiometer shown schematically in FIG. 4B.

Although the invention has been described in conjunction with specific embodiments thereof, it is evident that many alternatives, modifications and variations will be apparent to those skilled in the art. Accordingly, it is intended to embrace all such alternatives, modifications, and variations that fall within the spirit and broad scope of the appended claims.

What is claimed is:

1. A system for sensing water status in soil comprising:
    a porous material selected for actively proliferating root growth and having an area of at least 0.025 m²; and
    a water status sensor that is coupled to the porous material;
    wherein a first portion of the porous material is selected to have a hydraulic conductivity between 0.1-0.01 cm/hour within a matric head range of 0 to −500 cm $H_2O$ respectively and a second portion of the porous material is selected to have a hydraulic conductivity between 50-0 cm/hour within a matric head range of 0 to −50 cm $H_2O$ respectively, wherein the first portion and the second portion are formed from two different materials that are coupled to each other or the first portion is formed based on compacting the porous material with rolling or folding.

2. The system of claim 1, wherein the porous material is woven geotextile.

3. The system of claim 1, wherein the porous material is unwoven geotextile.

4. The system of claim 1, wherein the porous material is a strip of material with dimensions of 25-130 cm long and 2-50 cm wide.

5. The system of claim 1, wherein size of pores of the porous material is selected to decrease density of soil when positioned in the soil.

6. The system of claim 1, wherein the porous material is at least one of soaked in a liquid solution in which fertilizer is dissolved, impregnated with fertilizer in the form of granulates housed within pores of the porous material and impregnated with fertilizer in the form of hydrogel including liquid or granular or slow release fertilizer.

7. The system of claim 1, wherein the porous material is formed with pockets configured for holding fertilizer.

8. The system of claim 1, wherein the water status sensor is positioned in a pocket formed in the porous material.

9. The system of claim 1, wherein the water status sensor is soil matric potential sensor or soil water content sensor.

10. The system of claim 9, wherein the soil matric potential sensor comprises:
a porous cup;
a water filled tube;
a sensor; and
probe extending from the sensor toward the porous cup, wherein the probe is configured to sample the water at a height below a height at which bubbles accumulate in the water filled tube.

11. The system of claim 9, wherein the soil matric potential sensor comprises:
a porous cup;
a water filled tube;
a sensor;
a bridge shaped channel configured to provide fluid communication between the water filled tube and the sensor, wherein the bridge shaped channel is integrated with the tube and with a column extending from a peak height of the bridge, wherein the column is at a height above the sensor, and wherein the bridge shape channel is shaped as an arc with the column extending from the peak height of the arc or is shaped as an upside down Y and is configured to be filled with water.

12. The system of claim 1, wherein the water status sensor is tensiometer and is configured to operate without connection to an external water reservoir.

13. The system of claim 1, wherein the water status sensor is a remote sensor that is configured to sense the water status of the porous material without physical contact with the porous material.

14. The system of claim 1, wherein the water status sensor is configured to sense an average reading of the water status over the porous material.

15. A method for sensing water status in soil comprising:
laying a porous material selected for actively proliferating root growth and having an area of at least 0.025 m$^2$ on the soil; and
hydraulically coupling a water status sensor to the porous material or sensing the water status of the porous material without physical contact with the porous material.

16. The method of claim 15, wherein the porous material is selected to have a hydraulic conductivity that is higher than an average hydraulic conductivity of the soil and between 0.01-50 cm/hour.

17. The method of claim 15, wherein a first portion of the porous material is selected to have a hydraulic conductivity between 0.1-0.01 cm/hour within a matric head range of 0 to −500 cm $H_2O$ respectively and a second portion of the porous material is selected to have a hydraulic conductivity between 50-0 cm/hour within a matric head range of 0 to −50 cm $H_2O$ respectively, wherein the first portion and the second portion are formed from two different materials that are coupled to each other or the first portion is formed based on compacting the porous material with rolling or folding.

18. The method of claim 15, wherein the porous material is geotextile.

19. The method of claim 15, comprising at least one of soaking the porous material in a liquid solution or slow release fertilizer in which the fertilizer is dissolved and impregnating the porous material with fertilizer.

20. The method of claim 15, wherein the porous material is laid at depth of 5-50 cm under a surface of the soil and in a row over which cultivated plants are configured to be planted.

21. The method of claim 15, wherein the porous material is laid over an emitter configured to emit water for irrigating the soil.

22. The method of claim 15, wherein the water status sensor is a tensiometer that is a soil matric potential sensor or soil water content sensor.

23. The method of claim 15, wherein the water status sensor is configured to sense an average reading of the water status over the porous material.

24. A sheet material configured to sample average water status of soil over a spatial area, the sheet material comprising:
a first portion selected to have a hydraulic conductivity between 0.1-0.01 cm/hour within a matric head range of 0 to −500 cm $H_2O$ respectively; and
a second portion selected to have a hydraulic conductivity between 50-0 cm/hour within a matric head range of 0 to −50 cm $H_2O$ respectively, wherein the first portion and the second portion are coupled to each other.

25. The sheet material of claim 24, wherein the first portion and the second portion are formed from two different materials, wherein the first portion is formed based on compacting the sheet material in a roll or in a fold or wherein the first portion has a tighter weave as compared to the second portion.

26. A system for sensing water status in soil comprising:
a porous material selected for actively proliferating root growth and having an area of at least 0.025 m$^2$; and
a water status sensor that is coupled to the porous material;
wherein the porous material is at least one of soaked in a liquid solution in which fertilizer is dissolved, impregnated with fertilizer in the form of granulates housed within pores of the porous material and impregnated with fertilizer in the form of hydrogel including liquid or granular or slow release fertilizer.

27. A system for sensing water status in soil comprising:
a porous material selected for actively proliferating root growth and having an area of at least 0.025 m$^2$; and
a water status sensor that is coupled to the porous material;
wherein the porous material is formed with pockets configured for holding fertilizer.

28. A system for sensing water status in soil comprising:
a porous material selected for actively proliferating root growth and having an area of at least 0.025 m$^2$; and
a water status sensor that is coupled to the porous material;
wherein the water status sensor is tensiometer and is configured to operate without connection to an external water reservoir.

29. A system for sensing water status in soil comprising:
a porous material selected for actively proliferating root growth and having an area of at least 0.025 m$^2$; and
a water status sensor that is coupled to the porous material;

wherein the water status sensor is soil matric potential sensor, which comprises:

a porous cup;

a water filled tube;

a sensor; and probe extending from the sensor toward the porous cup, wherein the probe is configured to sample the water at a height below a height at which bubbles accumulate in the water filled tube.

30. A system for sensing water status in soil comprising:

a porous material selected for actively proliferating root growth and having an area of at least 0.025 m$^2$; and a water status sensor that is coupled to the porous material;

wherein the water status sensor is soil matric potential sensor, which comprises:

a porous cup;

a water filled tube;

a sensor; and a bridge shaped channel configured to provide fluid communication between the water filled tube and the sensor, wherein the bridge shaped channel is integrated with the tube and with a column extending from a peak height of the bridge, wherein the column is at a height above the sensor, and wherein the bridge shape channel is shaped as an arc with the column extending from the peak height of the arc or is shaped as an upside down Y and is configured to be filled with water.

* * * * *